United States Patent
De Viterbo

(10) Patent No.: US 9,724,068 B2
(45) Date of Patent: *Aug. 8, 2017

(54) METHOD FOR MEASURING INTRACRANIAL ELASTICITY

(71) Applicant: Arthur Rappaport, Stanford, CT (US)

(72) Inventor: Vitor Daniel De Viterbo, Belo Horizonte-MG (BR)

(73) Assignee: Arthur Rappaport, Stanford, CT (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/707,880

(22) Filed: May 8, 2015

(65) Prior Publication Data

US 2016/0095574 A1    Apr. 7, 2016

Related U.S. Application Data

(63) Continuation of application No. 13/381,632, filed as application No. PCT/US2009/052263 on Jul. 30, 2009, now Pat. No. 9,028,416.

(60) Provisional application No. 61/084,827, filed on Jul. 30, 2008.

(51) Int. Cl.
*A61B 8/00* (2006.01)
*A61B 8/08* (2006.01)
*A61B 5/03* (2006.01)
*A61B 5/00* (2006.01)

(52) U.S. Cl.
CPC ............ *A61B 8/0808* (2013.01); *A61B 5/031* (2013.01); *A61B 5/4064* (2013.01); *A61B 8/485* (2013.01); *A61B 8/5223* (2013.01); *A61B 5/7267* (2013.01)

(58) Field of Classification Search
CPC ... A61B 8/0808; A61B 8/5223; A61B 5/4064; A61B 5/031; A61B 8/485; A61B 5/7267
USPC .................................................. 600/437–469
See application file for complete search history.

(56) References Cited

U.S. PATENT DOCUMENTS

| | | | | |
|---|---|---|---|---|
| 5,840,018 A * | 11/1998 | Michaeli | ............. | A61B 8/0816 600/300 |
| 6,328,694 B1 * | 12/2001 | Michaeli | ................ | A61B 5/031 600/438 |
| 6,475,147 B1 * | 11/2002 | Yost | ........................ | A61B 5/031 600/438 |
| 6,702,743 B2 * | 3/2004 | Michaeli | ................ | A61B 5/031 600/438 |
| 8,926,515 B2 * | 1/2015 | Ragauskas | ............. | A61B 5/031 600/438 |
| 2003/0013956 A1 * | 1/2003 | Michaeli | ................ | A61B 5/031 600/437 |
| 2003/0060711 A1 * | 3/2003 | Michaeli | ................ | A61B 5/031 600/451 |

* cited by examiner

*Primary Examiner* — Sanjay Cattungal
(74) *Attorney, Agent, or Firm* — Gottlieb, Rackman & Reisman, PC

(57) ABSTRACT

A novel method to noninvasively measure intracranial pressure (ICP) and more generally brain elasticity is disclosed. ICP is determined using an algorithm coupled on a simulated artificial neural network (SANN) that calculates ICP based on a determination of a set of interacted ultrasound signals (IUSs) generated from multiple ultrasound pulses. The methods and systems of the present invention are capable of rapidly determining ICP without manual review of EPG waves by a technician.

13 Claims, 10 Drawing Sheets

1. EXAMPLE

1. If the machine is trained on nine patients:

Three patients with ICP=8mmHg (MEAN)
    Three patients with ICP=8.5mmHg ( " )
    Three patients with ICP=9.0mmHg ( " )
    TOTAL NINE PATIENTS 2. The operating range will be between 8 and 9mmHg

FIG. 9

METHOD FOR MEASURING INTRACRANIAL ELASTICITY

CROSS-REFERENCE TO RELATED APPLICATIONS

This application is a continuation of U.S. application Ser. No. 13/381,632 filed Dec. 29, 2011, now allowed, which is a National Phase of PCT/US 09/052263 which claims benefit of U.S. Provisional Patent Application No. 61/084,827 filed Jul. 30, 2008, which are hereby incorporated by reference as part of the present disclosure.

FIELD OF THE INVENTION

The present invention relates to a method for non-invasively measuring intracranial pressure.

BACKGROUND OF THE INVENTION

Generally, mammals such as humans have a constant intracranial volume of blood and, therefore, a constant intracranial pressure ("ICP"). A variety of normal and pathological conditions, however, can produce changes in intracranial pressure. Elevated intracranial pressure can reduce blood flow to the brain and in some cases can cause the brain to become mechanically compressed, and ultimately herniate. The most common cause of elevated intracranial pressure is head trauma. Additional causes of elevated intracranial pressure include, but are not limited to shaken-baby syndrome, epidural hematoma, subdural hematoma, brain hemorrhage, meningitis, encephalitis, lead poisoning, Reye's syndrome, hypervitaminosis A, diabetic ketoacidosis, water intoxication, brain tumors, other masses or blood clots in the cranial cavity, brain abscesses, stroke, ADEM ("acute disseminated encephalomyelitis"), metabolic disorders, hydrocephalus, and dural sinus and venous thrombosis. Because changes in intracranial pressure require constant monitoring and possible surgical intervention, the development of techniques to monitor intracranial pressure remains an important goal in medicine. U.S. Pat. No. 6,875,176.

Conventional intracranial pressure monitoring devices include: epidural catheters; subarachnoid bolt/screws; ventriculostomy catheters; and fiberoptic catheters. All of these methods and systems are invasive, and require invasive surgical procedures by highly trained neurosurgeons. Moreover, none of these techniques are suited to rapid or regular monitoring of intracranial pressure. In addition, all of these conventional techniques measure ICP locally, and presumptions are made that the local ICP reflects the whole brain ICP. The teachings of U.S. Pat. No. 6,875,176 illustrate these limitations of the existing methods.

There are no widely accepted methods of non-invasively measuring ICP. Clinically, however, the development of an effective means of measuring ICP is very important as ICP can be predictive of clinical outcome, and can lead to altered, more effective therapy. For example, after traumatic brain injury, intracranial pressure tends to rise requiring both prompt recognition and treatment. Zanier et al. *Critical Care* 11:R7 ("2007"). The existing standards in measuring ICP require direct, invasive measurement involving the placement of epidural transducers or intraventricular or intraparenchymatous catheters. Frank et al. *Zentralbl Neurochir* 61("4"): 177-80 ("2000"). The use of invasive methods increases the risk of injury from infection, bleeding or surgical mishap. Czosnyka et al. *J. Neurol. Neurosurg. Psychiatry* 75: 813-821 ("2004").

A variety of different techniques for noninvasively measuring ICP have been explored, including, measuring otoacoustic emissions ("Frank et al. *Zentralbl Neurochir* 61("4"): 177-80 ("2000")"), and ultrasound with a transcranial Doppler (Ragauskas et al. Innovative non-invasive method for absolute intracranial pressure measurement [online], [retrieved on Jul. 30, 2008]. Retrieved from the Internet <URL: http://www.neurosonology.org/bern2002/abs_12.html>).

For example, U.S. Pat. No. 6,702,743 ("the '743 patent") discloses a non-invasive means of measuring ICP. An ultrasound probe is placed on the head of a patient, and is then used to generate an ultrasound pulse which propagates through the skull and brain of the patient. The ultrasound pulse is reflected off of the skull and soft tissue lying in a path perpendicular to the ultrasound probe. A portion of a generated Echo EG signal is then selected, and the Echo EG signal is integrated over the selected portion to generate an echopulsograph ("EPG") signal. However, in order to determine ICP using the methods of the '743 patent, the operator must manually select, or "gate" a portion of the EPG and then review the EPG waveforms at each gate to determine which provides the optimal EPG waveform for a site of interest in the brain.

We have developed a novel method to noninvasively measure ICP and more generally brain elasticity that requires no manual review of EPG waves by a technician. ICP is determined using an algorithm coupled on a simulated artificial neural network ("SANN") that calculates ICP based on a determination of a set of interacted ultrasound signals ("IUSs") generated from multiple ultrasound pulses. The methods and systems of the present invention are capable of rapidly determining ICP without manual review of EPG waves.

SUMMARY OF THE INVENTION

It is an object of the present invention to provide a non-invasive technique for measuring ICP based upon the analysis of reflected ultrasound signals represented in echopulsograph ("EPG") form.

ICP is measured by first transmitting an ultrasound pulse of about at least 1 MHz into the cranium of a patient. This ultrasound pulse is then reflected by various structures in the cranium, including the walls of the third ventricle. The reflected signals are received by a transducer, and a package of information is generated.

The invention obtains multiple ultrasound signals of a patient. Since the state of the walls of the third ventricle are constantly changing due to blood flow into and out of the brain ("systole and diastole"), the computer is able to compare each signal to locate the region of the third ventricle based upon deviations in the respective waveforms.

Once the third ventricle is located, data points along the portion of the wave inside the third ventricle are used to calculate ICP. The ICP value is calculated from an algorithm that correlates the sampled values with ICP data derived from patients with known ICP values. The calculation is completed automatically by the computer once the system has been compared or trained by reference to known ICP values.

BRIEF DESCRIPTION OF THE DRAWINGS

FIG. 9 depicts an example of how the training process creates the range of measurable ICP values.

DETAILED DESCRIPTION

The present invention is directed to a method for non-invasively measuring ICP and more generally the elasticity of tissues within or proximate to various organs or cavities within the body. In one embodiment, ICP is determined by insonating the cranial cavity using a transcranial Doppler signal. First, the position of the anterior and posterior walls of the third ventricle are identified, and an ICP wave plot established. The ICP is then calculated from the ICP wave using a neural network. More generally, the methods and systems of the present invention may be used for measuring tissue elasticity in a variety of different tissues.

In one embodiment of the invention, the methods and systems of the present invention use ultrasonic probes. Such probes may be constructed from one or more piezoelectric elements activated by electrodes, for example, from lead zirconate titanate ("PZT"), polyvinylidene diflouride ("PVDF"), PZT ceramic/polymer composite, and the like. The electrodes are connected to a voltage source, a voltage waveform is applied, and the piezoelectric elements change in size at a frequency corresponding to that of the applied voltage. When a voltage waveform is applied, the piezoelectric elements emit an ultrasonic wave into the media to which it is coupled at the frequencies contained in the excitation waveform. Conversely, when an ultrasonic wave strikes the piezoelectric element, the element produces a corresponding voltage across its electrodes. The invention may be practiced using any of numerous ultrasonic probes that are well known in the art.

Figure 2:
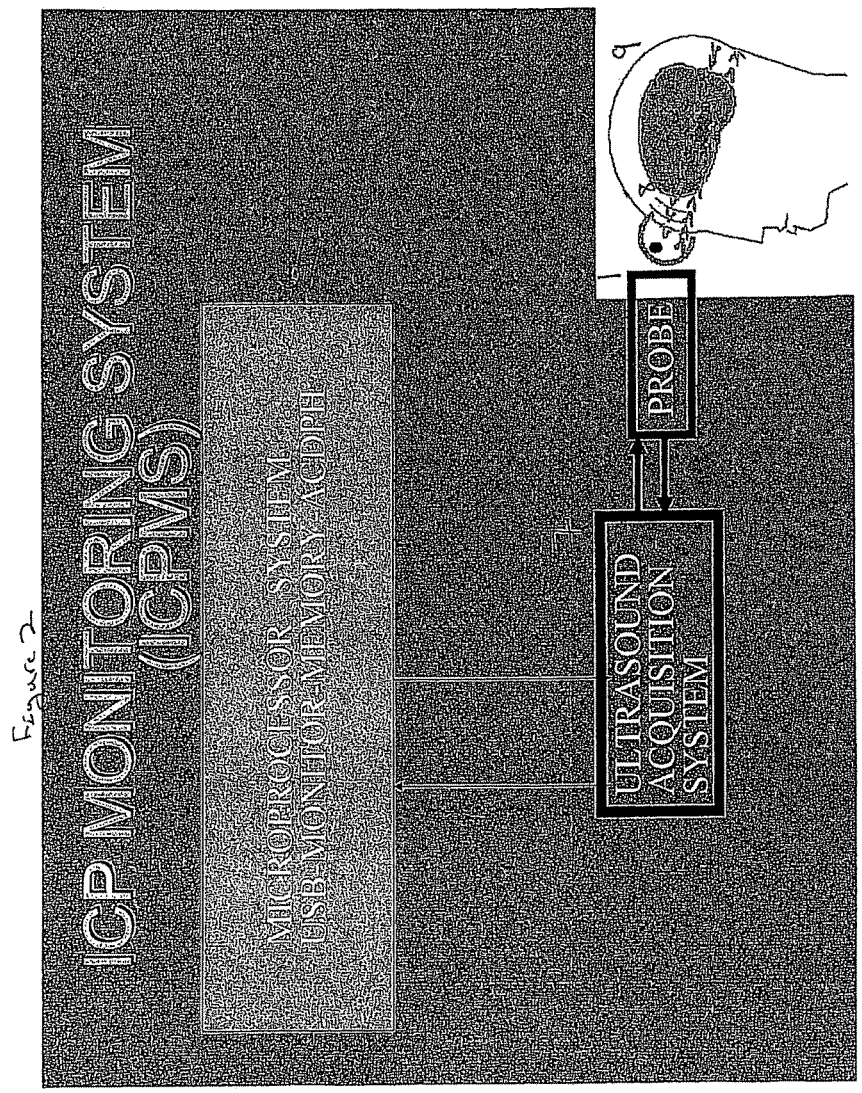
FIG. 2 depicts a flow chart of the intracranial pressure monitoring system.

FIG. 2 provides an overview of the methods of the invention. An ultrasound probe 1, transmits an ultrasound wave into the cranial cavity. The ultrasound probe is placed on the head of a patient, and is then used to generate an ultrasound pulse which propagates through the skull and brain of the patient. The ultrasound pulse is reflected off of the occipital portion of the cranium 9 as well as off of other semi-rigid or rigid structures encountered during transit across the brain tissue 8. One such structure that is encountered by the ultrasound pulse during transit is the third ventricle, including the anterior and posterior walls of the ventricle. The ultrasound pulse is reflected back to the ultrasound probe 1 to the ultrasound acquisition system 7. Any commercially available ultrasound apparatus may be used with the methods and systems of the present invention (see, Advanced Transducer Services, Inc. [online], [retrieved on Jul. 30, 2008]. Retrieved from the Internet <URL: www.atsultrasound.com/>). The signal can be interpreted by the microprocessor system with a loaded algorithm 6, which identifies the position of the third ventricular wall and correlates EPG points to an ICP value.

Figure 1:
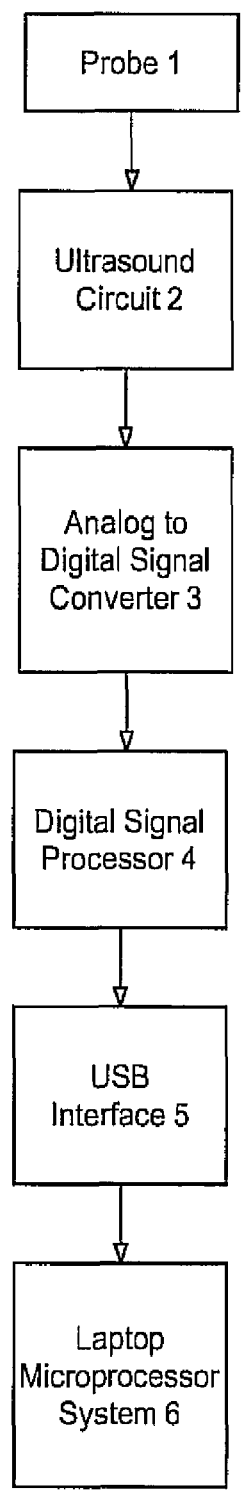
FIG. 1 depicts a block diagram of the preferred apparatus for transmitting and receiving ultrasound waves and training the artificial neural network.

FIG. 1 represents one embodiment of the system that can be used to measure the ICP. The system includes any central processing unit ("CPU") or microprocessor system, such as a laptop computer 6, a universal serial bus ("USB") interface 5, a digital signal processor ("DSP") 4, an amplifier, an analog to digital converter ("ADC") 3, an ultrasound circuit 2 and an ultrasound probe 1, having a transmitter, a receiver and a probe for generating the ultrasound pulse. The system is integrated with a means for measuring heart beats. It will be appreciated that the embodiment shown in FIG. 1 represents only one sample configuration of the system of the invention having a CPU 6, an analog to digital converter 3 and an ultrasound probe 1. All of these components are commercially available from standard electronic suppliers.

Standard, commercially available components may be used in system of the present invention. The following description of specific components is only exemplary, and the system of the present invention is not limited to these components. For example, the DSP 4 may be a C2000 DSC and TMS320C20x by Texas Instruments, a Canberra's 2060 model, CEVA-X1641, CEVA-X1622, CEVA-X1620, or the CEVA-TeakLite-III. The DSP 4 is responsible for generation of electrical pulses or signals with a frequency of at least 1 MHz via the probe 1, detection of the reflected waves or echoes through the probe 1, and processing of the detected digital signals. The ranges can be changed in the firmware of the DSP 4 according to the signal studied.

A measurement cycle is initiated when a start signal from the computer 6 is received by the DSP 4. In response, the DSP 4 instructs the probe 1 to generate a series of ultrasound pulses. A commercially available ultrasound probe may be used with the methods and systems of the invention (see, Advanced Transducer Services, Inc. [online], [retrieved on Jul. 30, 2008]. Retrieved from the Internet <URL: www.atsultrasound.com/>). The ultrasound probe 1 should be capable of transmitting ultrasound waves at a frequency of at least about 1 MHz, and up to about 10 MHz.

Ultrasound sources and detectors may be employed in a transmission mode, or in a variety of reflection or scatter modes, including modes that examine the transference of pressure waves into shear waves, and vice versa. Ultrasound detection techniques may also be used to monitor the acoustic emission ("s") from insonified tissue. Detection techniques involve measurement of changes in acoustic scatter such as backscatter, or changes in acoustic emission. Examples of acoustic scatter or emission data that are related to tissue properties include changes in the amplitude of acoustic signals, changes in phase of acoustic signals, changes in frequency of acoustic signals, changes in length of scattered or emitted signals relative to the interrogation signal, changes in the primary and/or other maxima and/or minima amplitudes of an acoustic signal within a cardiac and/or respiratory cycle; the ratio of the maximum and/or minimum amplitude to that of the mean or variance or distribution of subsequent oscillations within a cardiac cycle, changes in temporal or spatial variance of scattered or emitted signals at different times in the same location and/or at the same time in different locations, all possible rates of change of endogenous brain tissue displacement or relaxation, such as the velocity or acceleration of displacement, and the like. Multiple acoustic interrogation signals may be employed, at the same or different frequencies, pulse lengths, pulse repetition frequencies, intensities, and the multiple interrogation signals may be sent from the same location or multiple locations simultaneously and/or sequentially. Scatter or emission from single or multiple interrogation signals may be detected at single or at multiple frequencies, at single or multiple times, and at single or multiple locations.

Figure 3:
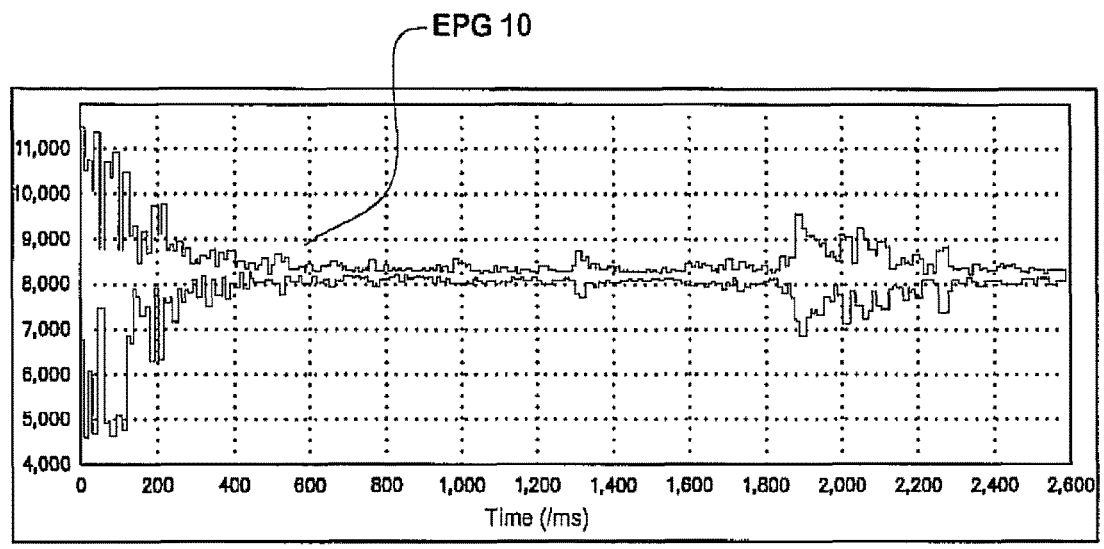
FIG. 3 depicts one full ultrasound reflected signal ("USRS").
Figure 4:
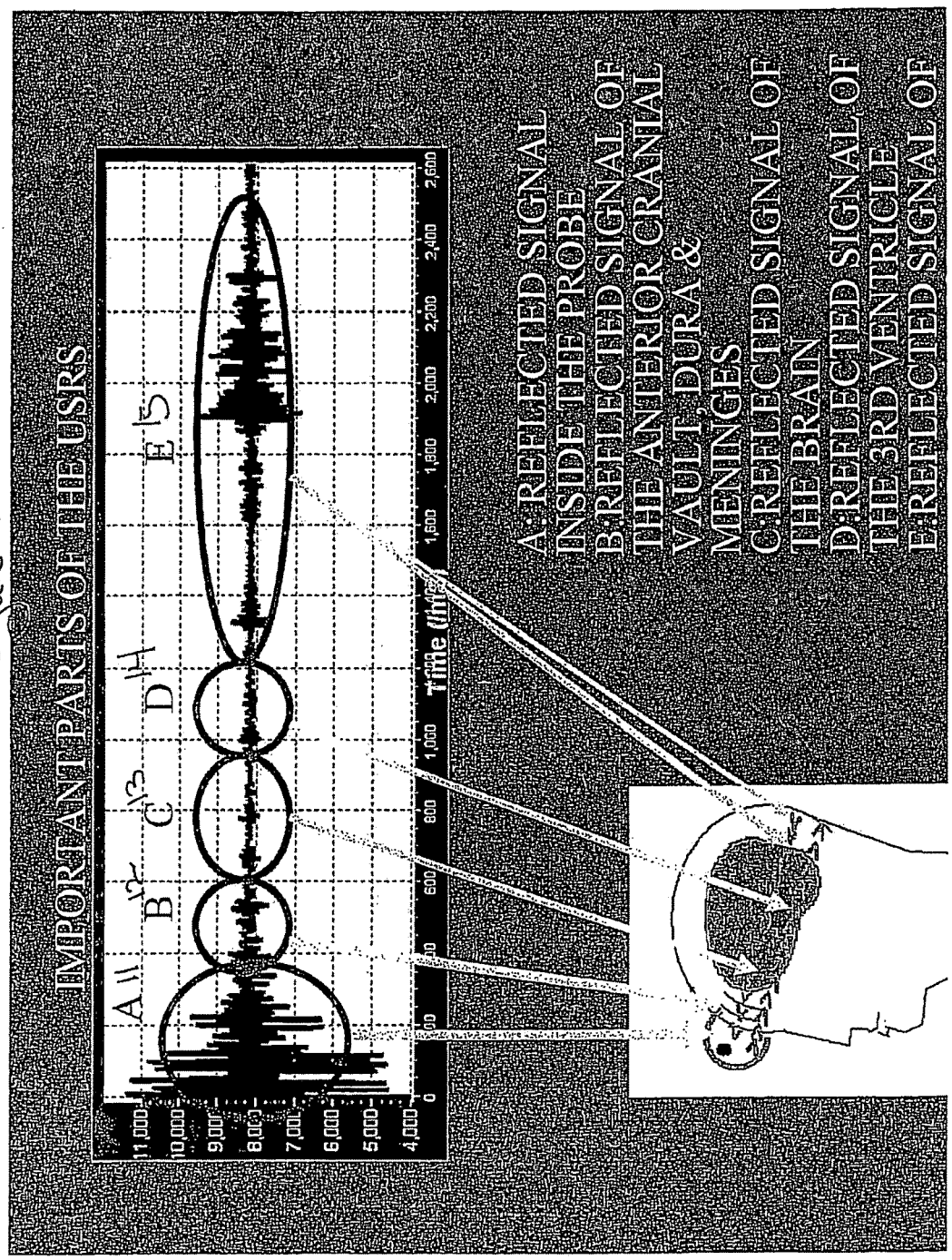
FIG. 4 depicts the correlation between parts of the USRS and the parts of brain.

FIG. 3 shows a single ultrasound reflected signal ("USRS"). Graphically, this ultrasound signal is referred to as an echopulsograph or EPG 10. It is an interactive signal that indicates the anatomic position of the anterior and posterior cranial vaults and the intracranial contents in the path of the ultrasound pulse. The ultrasound signals that insonate the brain, including the third ventricle, possess a certain frequency characteristic. If the return signal is unchanged, the EPG is merely measuring anatomic structures and reflecting back the same wave form. However, if the insonated ultrasound signal interacts with everything in its path, particularly the third ventricle dynamics, the resulting waveform or EPG is interactive and can be filtered to obtain a set of reflected signals to calculate ICP. For example, FIG. 4 is a labeled interactive EPG. The recognizable portions of the waveform correspond to reflected signals ("a") inside the probe 11, ("b") of the anterior cranial vault, dura and meninges 12, ("c") of the brain 13, ("d") of the third ventricle 14, and ("e") the reflected signal of dura and the posterior cranial vault 15.

Figure 7:
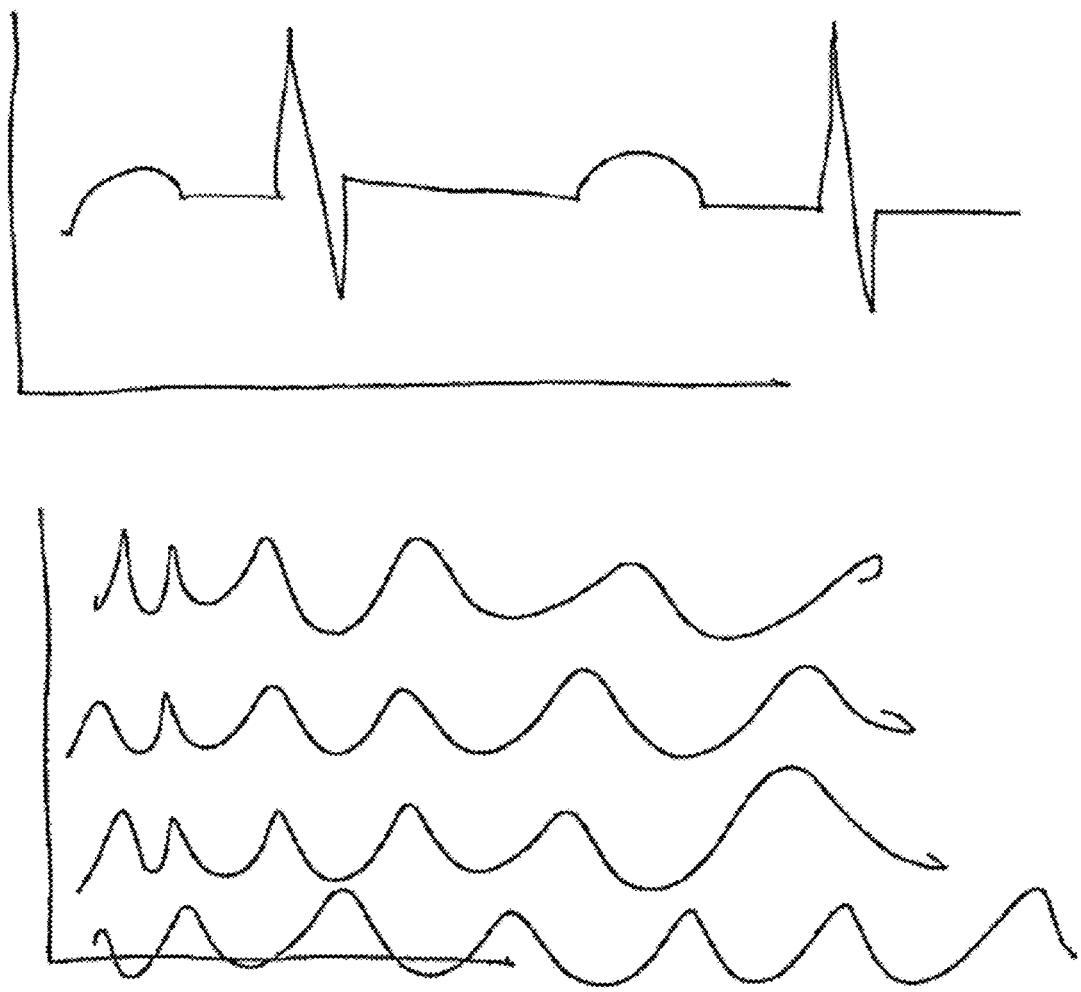
FIG. 7 is a side-by-side comparison a QRS complex and ultrasound signals.

During any cardiac cycle ("systole and diastole") multiple EPG measurements can be taken; FIG. 7 is a side-by-side comparison of EPGs and a QRS complex showing the relationship between the cardiac cycle and the brain. Walls of the third ventricle expand and contract during the cardiac cycle ("systole and diastole"). Therefore, the positions of the walls of the third ventricle vary relative to the ultrasound probe during the cardiac cycle.

Figure 5:
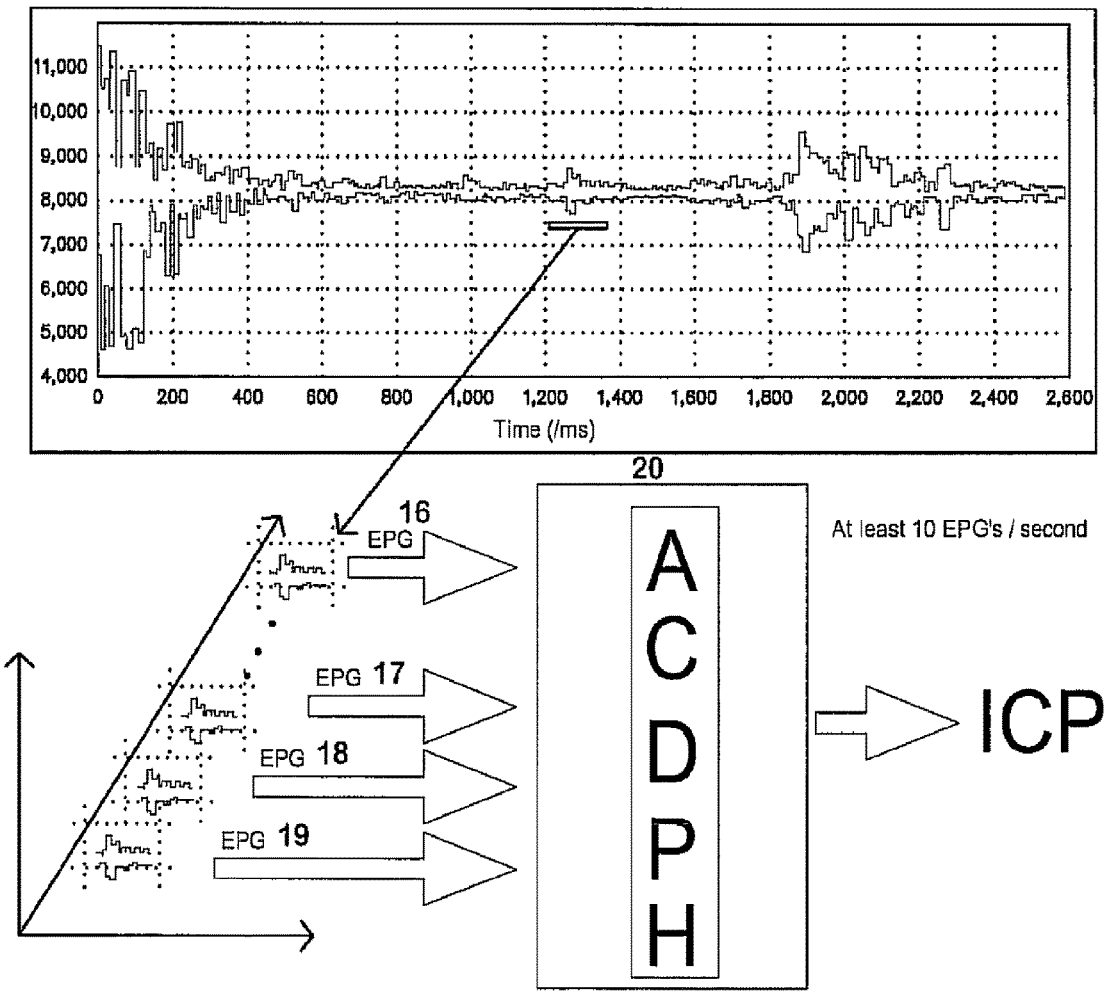
FIG. 5 depicts flow chart of inputting the USRS data points into the neural network and the algorithm to obtain an ICP value.
Figure 6:
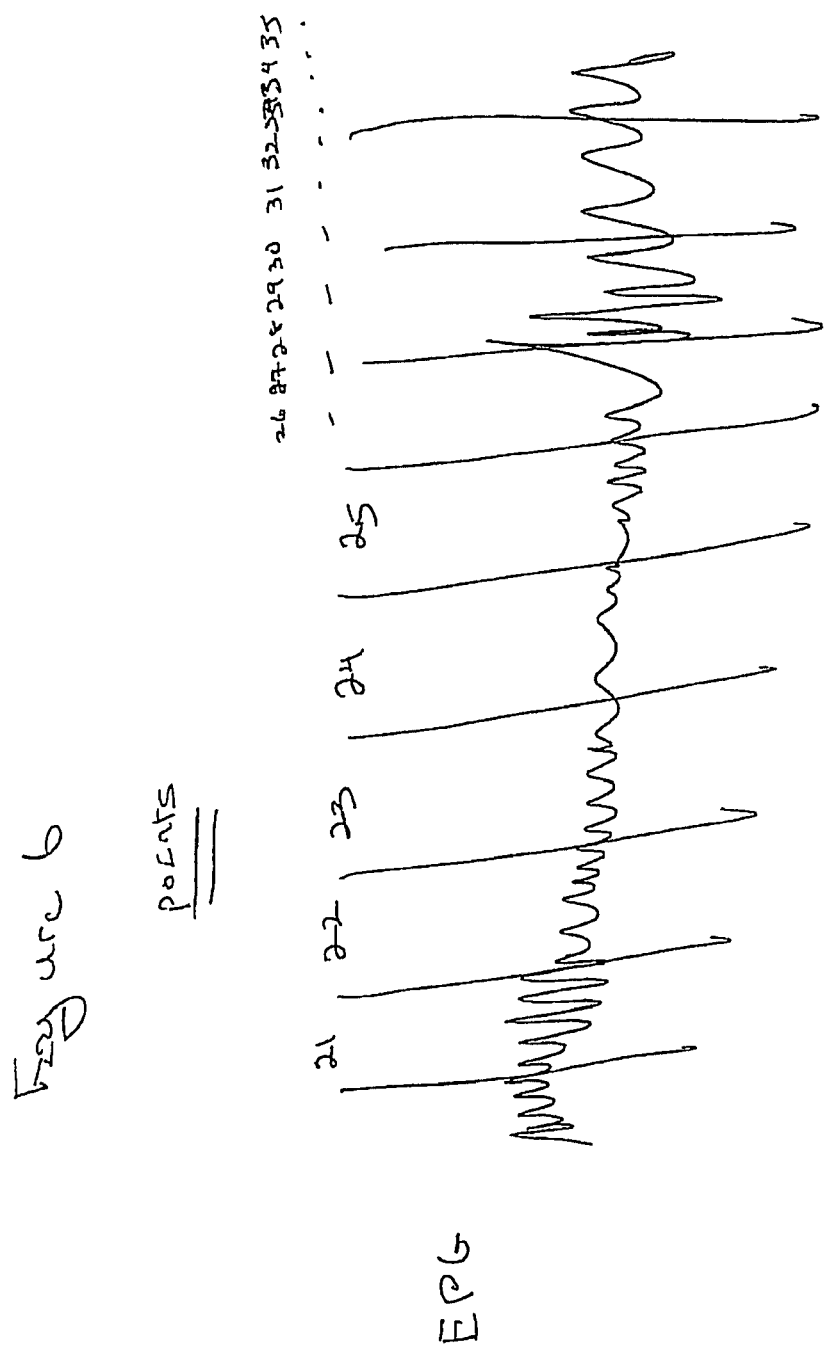
FIG. 6 depicts examples of the specific EPG points used as input.

In one embodiment of the invention, at least 10 EPGs measurements are made. In another embodiment, at least 25 EPGs are made. In a third embodiment, at least 50 EPGs are made. In a fourth embodiment, at least 100 EPGs are made. The EPG signals are each digitized and displayed on a display screen as a function of intensity and time. As shown in FIG. 5, points from the third ventricle region of all the EPGs 16-19 created are inputted into an algorithm to calculate an ICP value. These points are represented more clearly in FIG. 6, which depicts how the third ventricle region of an EPG is divided into insular points 21-35 over time ("t").

These points represent the discrete bundles of digitized data points from the isolated portion of the EPG, which are then used to calculate ICP based on the equation:

$$ICP = \Sigma \tan h("\Sigma^{I \times W + b"})W + b$$

where I represents the input matrix of all the data points from the selected portion of the echopulsogram 21-35, W is the weight matrix that is obtained through the training process, and b is a random bias constant assigned by the computer 6.

The input matrix is a ("n by k") mathematical matrix where n rows equals the number of samples; in one embodiment of this invention, this value is at least ten. The k columns equal the data points along the respective EPGs found between the ventricle walls. The matrix is calculated via known mathematical means.

Figure 8:
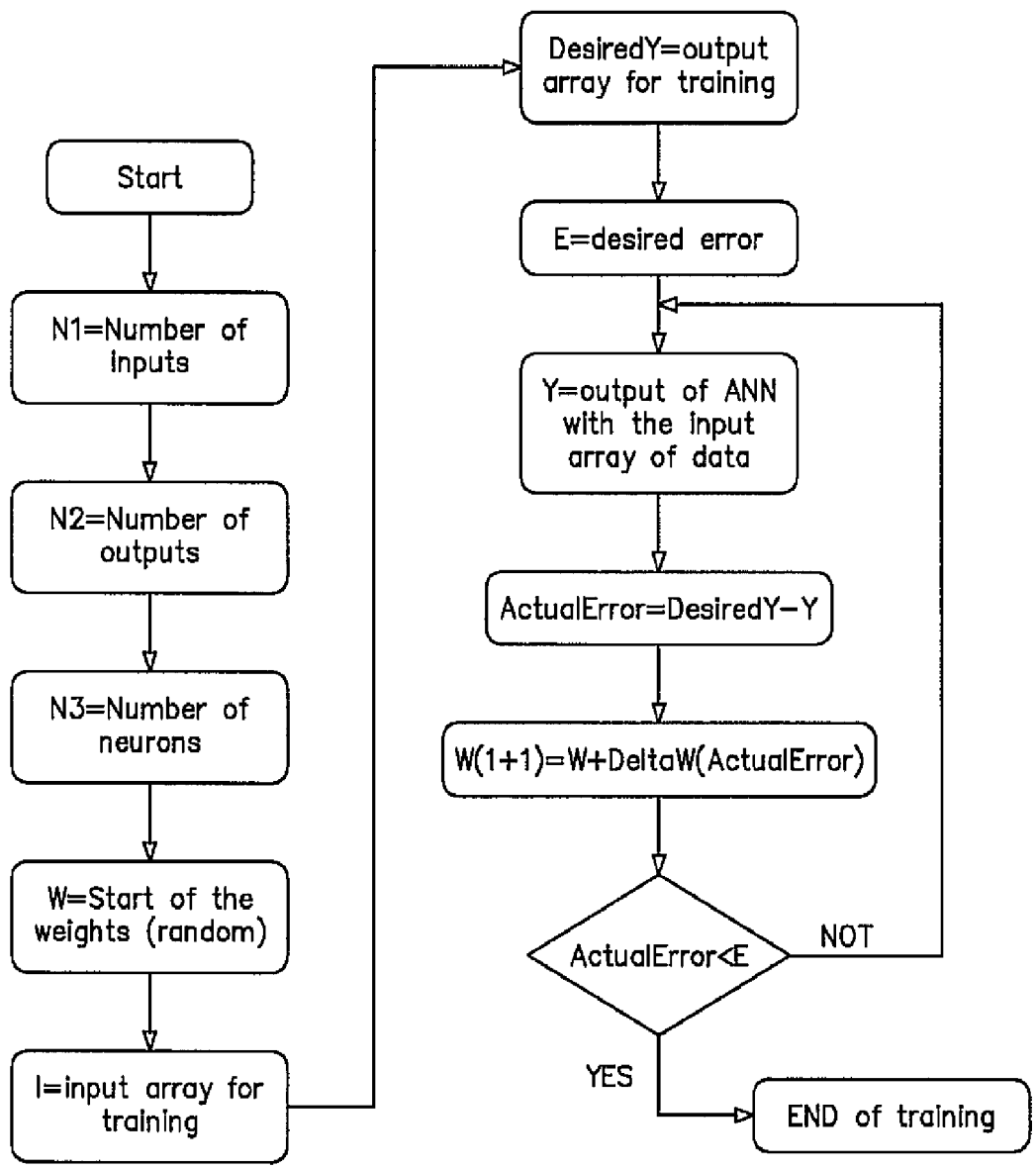
FIG. 8 depicts a flow chart of the back propagation method used in the training process.

The W value, or weight matrix, is obtained through the training or correlation process, which must be done once. The method of training the SANN is described in V. D. De Viterbo and J. C. Belchior, *Artificial Neural Networks Applied for Studying Metallic Complexes*, Journal of Computational Chemistry, vol. 22, no. 14, 1691-1701 ("2001"). The training process is a backpropagation algorithm that consists of repeatedly presenting the input and desired output sets to the network. The weights are gradually corrected until the desired error is achieved in the network. This method is depicted in FIG. 8. In one embodiment of the invention, the backpropagation method is carried out according to $$\Delta W^l_{ji} = \eta \delta^l_j \text{out}^{l-1}_i + \mu \Delta W^{l(previous)}_{ji} \quad (1)$$

where $\Delta W^l_{ji}$ represents the correction to the weight between the jth element in the lth layer and ith element in the previous layer. The quantity out$^{l-1}_i$ contains the output result on the l-1 layer. The parameters $\eta$ and $\mu$ are denominated the learning rate and the momentum constant, respectively. These constants determine the rate of convergence during the training procedure. Usually, these parameters are dynamically adjusted to obtain the best convergence rate. The errors introduced during the training stage are calculated as $$\delta^{last}_j = (y_j - \text{out}^{last}_j)\text{out}^{last}_j(1 - \text{out}^{last}_j) \boxtimes \quad (2)$$

and $$\delta^l_j = (\Sigma^r_{k=1} \delta kl + 1 \, Wkjl + 1) \boxtimes \text{out}^l_j(1 - \text{out}^l_j) \quad (3)$$

where $y_j$ is the output target that is compared with the output results of the out$^l_j$ of the lth layer. The network error can be then calculated as $$\epsilon^l = \Sigma^n_{j=1}(y_j - \text{out}^l_j)^2 \quad (4)$$

For the learning procedure the neuron behavior was calculated through the sigmoid function for the intermediary layer and a linear function in the output layer.

For minimizing functions, one embodiment of the invention uses the robust method proposed by Levenberg and implemented by Marquardt (Marquardt et al. *J Soc Ind Appl Math* 11:431 ("1963")). It works through the dynamical adjustment of the Steepest Descent method and Newton's method. Its advantage is that it is much faster in the way of finding the minimum. According to the Levenberg-Marquardt method (LMM), the update matrix of the weights can be calculated as $$W_{n+1} = W_n - (H + \beta I)^{-1} \nabla \epsilon^l(W_n) \quad (5)$$

where H is the Hessian matrix and $\beta$ is a variable parameter, and usually it starts as $\beta = 0.01$. The latter is changed during the minimization search according to the estimation of the local error, and I is the identity matrix. The most difficult task when the LMM is used can be attributed to the calculation of H, and it is approached by $$H = J^T J \quad (6)$$

where J is the Jacobian matrix and is given by $$J = \frac{\partial \epsilon l}{\partial \text{out}^L_j} \quad (7)$$

where l is the relative error of all weights [eq. (4)]. This approximation for solving the Hessian matrix will avoid computation of second derivatives, which simplifies the calculations. Substituting the above approaches into eq. (5), one obtains $$W_{n+1} = W_n - [J^T(W_n)J(W_n) + \beta_n I]^{-1} J^T(W_n)\epsilon^l(W_n) \quad (8)$$

Equation (8) will approach to the pure Gauss-Newton method if β→0 or to the Steepest descent method when β→∞.

In accordance with the present invention, this means that, initially, an ICP value is calculated via the equation with a randomly assigned W value. The resulting ICP value is the test value. A reference ICP value is determined by a known invasive means of measuring ICP. Training then involves comparing that test ICP value to the reference ICP value obtained from a known invasive method. If the difference in ICP values is greater than an acceptable error, the random W value is adjusted. Upon adjusting the W value, a new test ICP value is calculated using the equation and this value is again compared to the reference ICP value. This training process of adjusting the weight value, calculating a new ICP value and comparing it to a reference point is repeated until the calculated ICP value from this process is within an acceptable range of error to the reference value. When this occurs, the W value is stored by the computer 6 and automatically correlated to that specific ICP value that was obtained as the test ICP value. In one embodiment of the invention, the algorithm to train the neural network is as follows:

```
BEGIN
    WHILE START=ON
        GET SAMPLES OF DIGITALIZED ECHO FROM ADC
        STORE THE SAMPLES IN A FILE
        PLOT THE SAMPLES
        CHOOSE THE VALID WAVES (MANUAL PROCESS)
        IF WAVES ARE VALID
            START=OFF (MANUAL)
        END IF
    END WHILE
    NUMBERS OF INPUT OF THE NEURAL NETWORK=306
    NUMBERS OF HIDDEN NEURONS=2
    W1(2×306)=RANDOM NUMBERS
    W2(1×2)=RANDOM NUMBERS
        WHILE(ERROR>0.001)
            ICP_NON_INVASIVE=
                W2*(TANH(W1*DIGITALIZED_ECHO))
            ERROR=ICP_INVASIVE − ICP_NON_INVASIVE
            CALCULATE THE NEW W1 AND W2 USING THE
            LEVENBERG MARQUARDT METHOD
            W1=W1+DW1
            W2=W2+DW2
        END WHILE
END BEGIN
```

This training process must be completed for each possible ICP value for the computer to create an index or database of weight values and corresponding ICP values. After the training, the computer 6 is able to calculate the ICP values automatically by corresponding the appropriate W value for each set of inputs and ICP value without an invasive procedure. FIG. 9 illustrates how the training process expands the range of possible measured ICP values. Obtaining the ICP values of 9 patients, 3 groups of 3, with 3 different ICP values and inputting their would be ultrasound data into the invention as an initial matter provides the invention with a baseline for comparison. The operating range of the invention would also be equal to the range of the known ICP values it was trained on.

The neural network is, therefore, an Algorithm for Correlation of Dynamic Properties of the Head ("ACDPH") 20. It creates ICP waves using the inputted data. Each point at time ("t") along the EPG wave is then plotted across multiple EPG waves. As can be appreciated, up to ("n") samples can be made from a single EPG wave. A graph is then prepared for each time ("t") showing the amplitude of the EPG wave at each time ("t") for multiple EPG waves. For structures, such as the occipital portion of the cranium, which do not vary over the cardiac cycle, the graph showing the sampling from multiple EPG waves at time ("t") is a straight line. The same is not true of points along the third ventricle. Graphically, this is reflected by a change in amplitude in the EPG wave during the cycle. More specifically, this change is represented as an ICP wave with a sine wave pattern, reflecting the expansion and contraction of the wall over the cardiac cycle. The ADCPH 20 obtains the upper and lower boundaries of the inputted points and correlates that data with the value of patients' ICPs obtained from an invasive device through training. After training, the ADCPH is able to calculate the ICP of the patient automatically without using an invasive method. In one embodiment of the invention, the algorithm to obtain the ICP values is as follows:

```
BEGIN
    WHILE START=ON
        LOAD TRAINED NEURAL NETWORK W1 AND W2
        GET SAMPLES OF DIGITALIZED ECHO FROM ADC
        STORE THE SAMPLES IN A FILE
        PLOT THE SAMPLES
        CHOOSE THE VALID WAVES (MANUAL PROCESS)
        IF WAVES ARE VALID (MANUAL PROCESS)
            ICP_NON_INVASIVE=
                W2*(TANH(W1*DIGITIZED_ECHO))
        END IF
    END WHILE
END BEGIN
```

Figure 10:
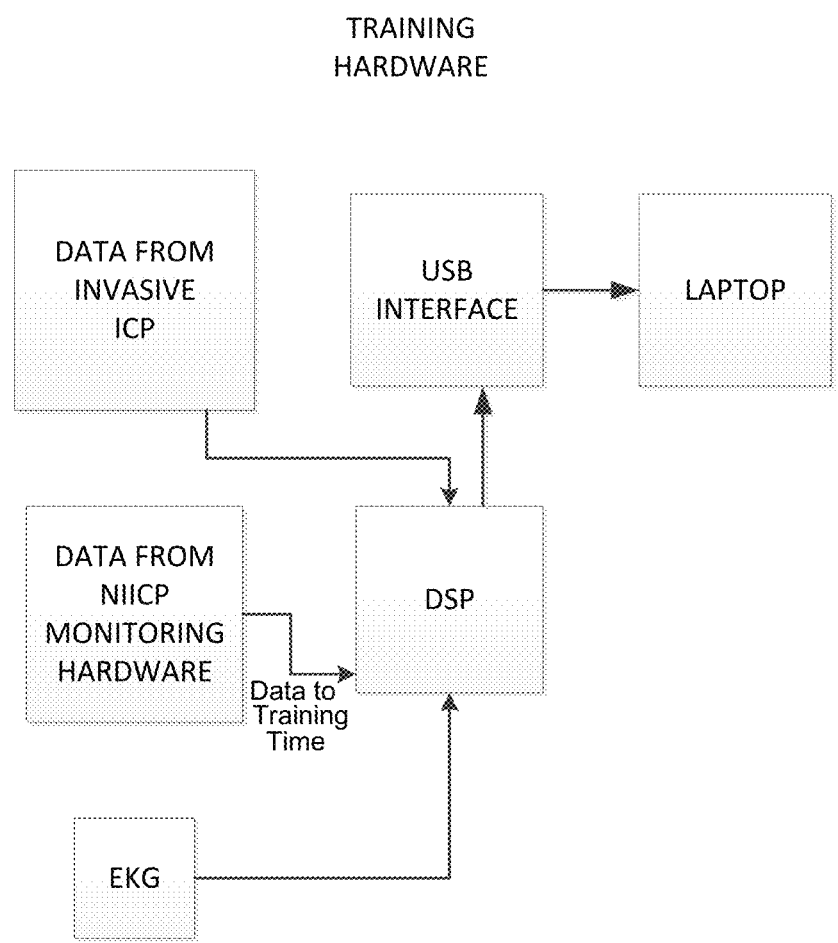
FIG. 10 depicts an embodiment of the hardware for the training process.

FIG. 10 depicts one embodiment of the hardware for the instant training process. The data from the invasive ICP monitoring hardware, the data from the non-invasive ICP monitoring hardware, and the electrocardiogram (EKG) data are inputted into the DSP, which is then connected to a laptop computer through a USB interface. For data output, in one embodiment of the invention, a laptop computer displays on its monitor the EPG, the EKG, and the calculated non-invasive ICP values.

In contrast to the '743 patent, the present invention provides a more accurate ICP measurement because it takes into account the changes over time in the third ventricle. The '743 patent relies on a point in time at which the flow of blood through the brain tissue is primarily exiting the brain. Moreover, after generating an EPG from an Echo EG signal and an ECG, the prior art patent relies on the operator to select the portion of the EPG that corresponds to the ICP value. In the present invention, the computer program identifies the relevant portion of the graph, the third ventricle. Last, the '743 patent calculates ICP based on an equation, $ICP = \rho("t/T") \cdot [t/T] - \beta$, that relies on four different equations to define $\rho("t/T")$.

The scope of the present invention is not limited by what has been specifically shown and described hereinabove. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. A method of measuring elasticity of a tissue within a mammalian body, comprising the steps of:
   a. transmitting at least one ultrasound pulse into the body at a target to obtain a reflected signal;
   b. graphing the reflected signal ("s") intensity over time ("t") to generate an echopulsograph ("EPG");
   c. identifying the points of variation of said signal over time; and
   d. calculating the elasticity of a tissue using said points of variation and a weighing function W;
wherein said weighing function W is obtained by performing the steps of:
   e. determining a reference value corresponding to an initial tissue elasticity as represented by an initial set of points of variation;
   f. assigning an arbitrary value for said weighing function W;
   g. calculating an intermediate value for a current tissue elasticity from said initial set of points of variation and said arbitrary value;
   h. calculating a difference between said reference value and said intermediate value;
   i. changing said arbitrary value of function W based on said difference; and
   j. repeating steps g and 1 until said intermediate value reaches said reference value.

2. The method of claim 1, wherein the ultrasound pulse has a frequency of at least 1 MHz.

3. The method of claim 1, wherein the ultrasound pulse has a frequency of at least 5 MHz.

4. The method of claim 1, wherein the ultrasound pulse has a frequency of at least 10 MHz.

5. The method of claim 1, wherein at least 10 ultrasound pulses are transmitted into the body.

6. The method of claim 1, where the ultrasound pulse has an amplitude between 0 to 200 volts.

7. The method of claim 1, where the ultrasound pulse is received by an ultrasound receiver at a rate of 10 mega-samples/sec over 14 beats.

8. The method of claim 1, where the ultrasound pulse is received by an ultrasound receiver at a rate of 1000 mega-samples/sec over 14 beats.

9. The method of claim 1, where the ultrasound pulse is received by an ultrasound receiver at a rate of 10,000 mega-samples/sec over 14 beats.

10. The method of claim 1, where the ultrasound pulse is received by an ultrasound receiver at a rate of 100,000 mega-samples/sec over 14 beats.

11. The method of claim 1 wherein said elasticity is calculating using the formula:

$$\Sigma \tan h(\Sigma l \times W + b) W + b$$

wherein l is an input matrix of data points based on the reflected signal(s), and b is a bias constant.

12. The method of claim 1 wherein said step of calculating said elasticity is performed using a neural network.

13. The method of claim 1 further comprising performing an invasive technique on said tissue to determine said reference value.

* * * * *